United States Patent
Nakayama et al.

(10) Patent No.: US 10,485,494 B2
(45) Date of Patent: Nov. 26, 2019

(54) HOLDING TRAY AND BUCKY IMAGE CAPTURING TABLE

(71) Applicant: Konica Minolta, Inc., Tokyo (JP)

(72) Inventors: Shingo Nakayama, Hino (JP); Takafumi Matsuo, Hino (JP)

(73) Assignee: Konica Minolta, Inc., Tokyo (JP)

( * ) Notice: Subject to any disclaimer, the term of this patent is extended or adjusted under 35 U.S.C. 154(b) by 136 days.

(21) Appl. No.: 15/871,198

(22) Filed: Jan. 15, 2018

(65) Prior Publication Data
US 2018/0214092 A1 Aug. 2, 2018

(30) Foreign Application Priority Data
Jan. 31, 2017 (JP) .................................. 2017-015086

(51) Int. Cl.
*A61B 6/00* (2006.01)
*A61B 6/04* (2006.01)
*A61B 6/08* (2006.01)

(52) U.S. Cl.
CPC .............. *A61B 6/0414* (2013.01); *A61B 6/08* (2013.01); *A61B 6/4233* (2013.01); *A61B 6/4283* (2013.01); *A61B 6/4411* (2013.01); *A61B 6/461* (2013.01); *A61B 6/465* (2013.01)

(58) Field of Classification Search
CPC ....... A61B 6/4283; A61B 6/42; A61B 6/4266; A61B 6/502; A61B 6/0414; G03B 42/04; G03B 42/045
See application file for complete search history.

(56) References Cited

U.S. PATENT DOCUMENTS 7,270,477 B1 * 9/2007 Kari ........................ G03B 42/04
378/167
2009/0092230 A1 * 4/2009 Hornig ................. G03B 42/025
378/98.8

FOREIGN PATENT DOCUMENTS

JP    H06-68730 U    9/1994
JP    2005-204857 A    8/2005

* cited by examiner

*Primary Examiner* — Don K Wong
(74) *Attorney, Agent, or Firm* — Osha Liang LLP

(57) ABSTRACT

A holding tray holds an X-ray detection panel on a placing surface. The holding tray includes: a lock that locks the X-ray detection panel on the placing surface with a plurality of holding patterns of different types and/or arrangement directions of the X-ray detection panel; and a detector that detects the holding pattern of the X-ray detection panel locked on the placing surface.

12 Claims, 11 Drawing Sheets

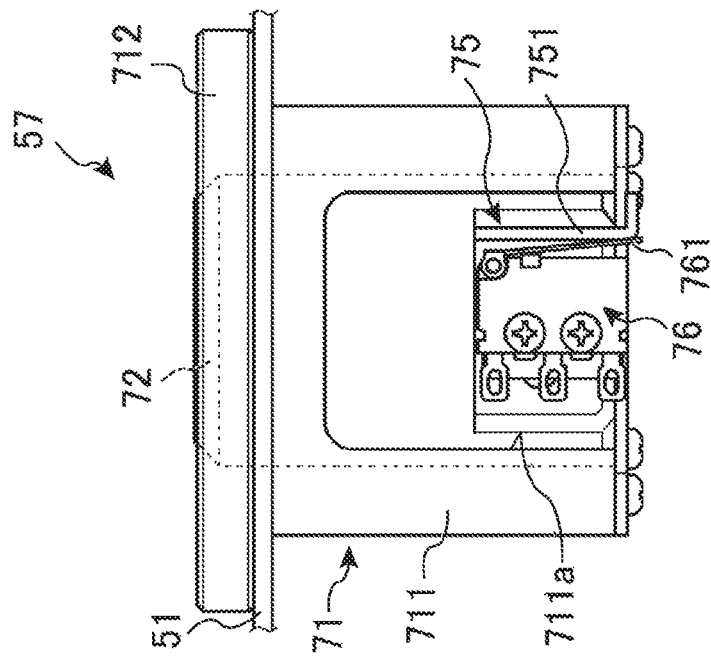
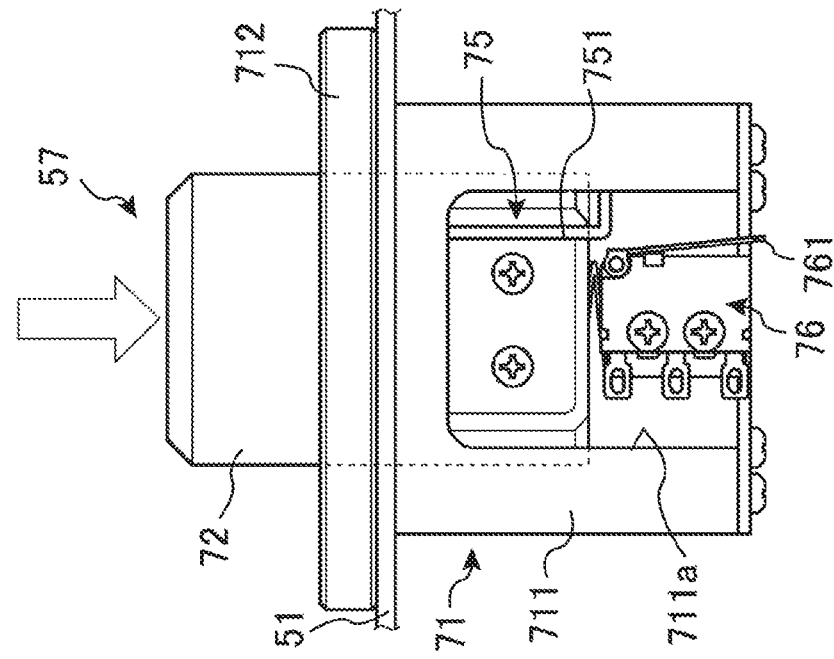

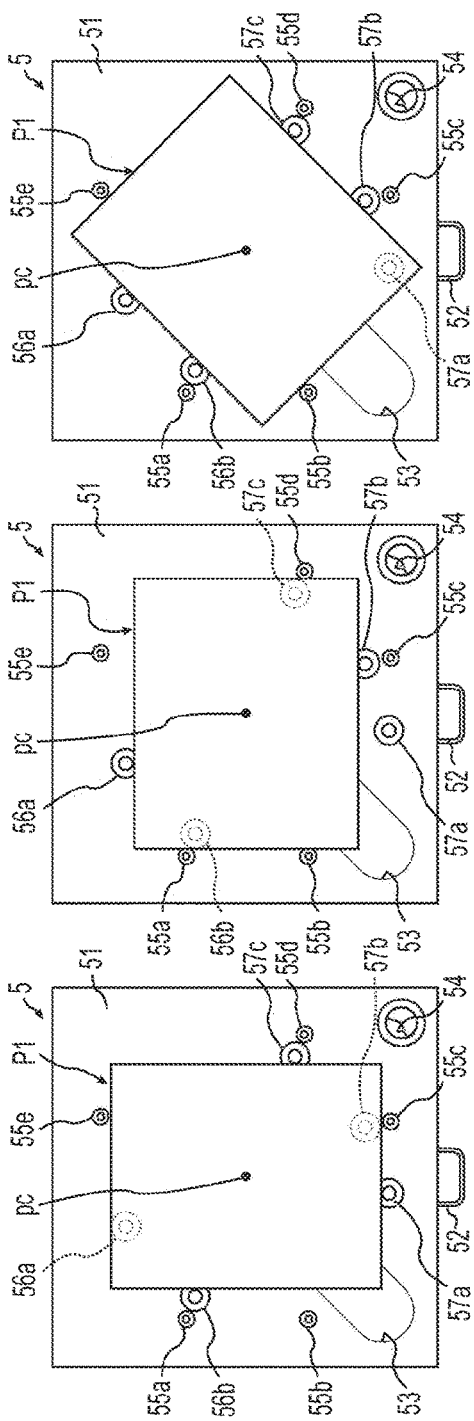

HOLDING TRAY AND BUCKY IMAGE CAPTURING TABLE

CROSS-REFERENCE TO RELATED APPLICATIONS

The entire disclosure of Japanese patent Application No. 2017-015086, filed on Jan. 31, 2017, is incorporated herein by reference.

BACKGROUND

Technical Field

The present invention relates to a holding tray and a bucky image capturing table.

Description of the Related Art

Radiation images captured using radiation represented by X-rays are widely used for the purpose of disease diagnosis and the like. Conventionally, such a medical radiation image has been captured, using a screen film, but a computed radiography (CR) apparatus using a stimulable phosphor sheet has been developed in order to digitize a radiation image. Recently, a radiation image capturing apparatus (Flat Panel Detector) has been developed which detects emitted radiation with a radiation detecting element to acquire the radiation image as digital image data.

In the CR apparatus, in many cases, a so-called CR cassette with a stimulable phosphor sheet or the like housed in a cassette-like housing is loaded on a bucky image capturing table and radiation image capturing is performed.

Also, in the radiation image capturing apparatus, in recent years, a portable radiation image capturing apparatus (hereinafter, such a portable radiation image capturing apparatus is referred to as an FPD cassette), in which radiation detecting elements and the like are housed in a housing and made portable, has been developed and put to practical use. Similarly to the CR cassette, such an FPD cassette can be loaded on a bucky image capturing table to perform the radiation image capturing.

In the radiation image capturing, an image capturing target needs to be within the image capturing region. In the existing image capturing apparatus, there is a situation in which, except for the long-length image capturing apparatus, it is possible to perform only the image capturing within the image capturing region depending on the size of the X ray detection panel such as a CR cassette or an FPD cassette.

In this respect, for example, when capturing an image of a human bone, the length of the longest femur in the human bone can be obtained in Japan in accordance with the following calculation formula (Kudo's calculation formula).

$$\text{Femur bone length} = (\text{height (cm)} - 56)/2.5$$

As a result, if it is desired to correspond to the length of a femur of human with a height of 100 cm to 180 cm, an image capturing region of 17.6 to 49.6 cm is necessary after considering the magnification ratio.

However, for example, the currently available FPD cassette has lengths of vertical and horizontal sides of 14 inches×17 inches or 17 inches×17 inches, and even if the size of 17 inches×17 inches is used, the image capturing region is 460 mm, and when it is desired to capture an image of the femur of a person having a height of 180 cm, the image capturing region will be insufficient.

Thus, JP 6-68730 Y discloses a configuration in which a freely rotatable turntable is provided under a top plate, a bucky (that is, a panel holding portion which holds an X-ray detection panel such as a CR cassette or an FPD cassette) is attached to an upper surface of the turntable, and the entire bucky is rotated.

Further, J P 2005-204857 A discloses a configuration that enables the image capturing by placing an X-ray detection panel on a top plate.

As disclosed in JP 6-68730 Y and JP 2005-204857 A, if the X-ray detection panel can be disposed in an arbitrary orientation, by obliquely disposing the X-ray detection panel, it is possible to keep the image capturing target with the length equal to or longer than the length of the vertical and horizontal sides of the X-ray detection panel within the image capturing range.

However, in the radiation image capturing, it is necessary to accurately match the position of the X-ray detection panel, the angle of the bulb, and the like.

Therefore, considering the actual operation, in the configuration disclosed in JP 6-68730 Y, in addition to a mechanism which rotatably holds the X-ray detection panel, there is a need for a rotation lock mechanism which locks the X-ray detection panel when performing the image capturing at the conventional regular angle (the position at which the X-ray detection panel is not rotated). Further, when the image capturing is performed at a position where the X-ray detection panel is not rotated, and when the image capturing is performed at an oblique position by rotating the X-ray detection panel, accurate angular information on the X-ray detection panel is required. Furthermore, when the image capturing is performed with the X-ray detection panel set at an arbitrary angle, means for adjusting the deviation of the angles of the bulbs is required, and the time required for the angle and position adjustment of the bulbs also increases.

Further, in the configuration described in JP 2005-204857 A, it is possible to accurately detect the position and angle of the X-ray detection panel and to perform the control accordingly, but when a control device is also included, the system scale becomes complicated.

In the clinical setting, there is a need for a configuration capable of capturing the image of the longest bone in the human body called femur.

However, when introducing a dedicated system such as a long-length image capturing apparatus or the like for that reason, the cost increases. Thus, it is desirable to set a range slightly larger than the panel size of 17 inches×17 inches, which is the maximum size of the conventional X-ray detection panel, to the image capturing range with a simple configuration, without introducing a special system.

SUMMARY and one or more embodiments of the present invention provide a holding tray and a bucky image capturing table capable of performing the image capturing at high precision and high quality with a simple configuration up to a range that does not fit in the image capturing region when the conventional X-ray detection panel is disposed vertically or horizontally.

According to one or more embodiments of the present invention, there is provided a holding tray which holds an X-ray detection panel on a placing surface, and the holding tray of one or more embodiments of the present invention comprises:

a lock capable of locking the X-ray detection panel on the placing surface with a plurality of holding patterns of different types and/or arrangement directions of the X-ray detection panel; and a detector capable of detecting the holding pattern of the X-ray detection panel locked on the placing surface.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 6A is a front view of the sensor in a state in which the X-ray detection panel is not placed according to one or more embodiments, and FIG. 6B is a front view of the sensor in a state in which the detection panel is placed according to one or more embodiments;

FIGS. 7A to 7C are plan views illustrating a positional relation between each arrangement direction of X-ray detection panel of 14×17 size, and a lock and a detector, and FIGS. 7D and 7E are plan views illustrating a positional relation between each arrangement direction of the X-ray detection panel of 17×17 size, and the lock and the detector, according to one or more embodiments;

DETAILED DESCRIPTION OF EMBODIMENTS

Hereinafter, embodiments of a holding tray and a bucky image capturing table provided with the holding tray will be described with reference to the drawings. However, the scope of the invention is not limited to the disclosed embodiments.

Figure 1:
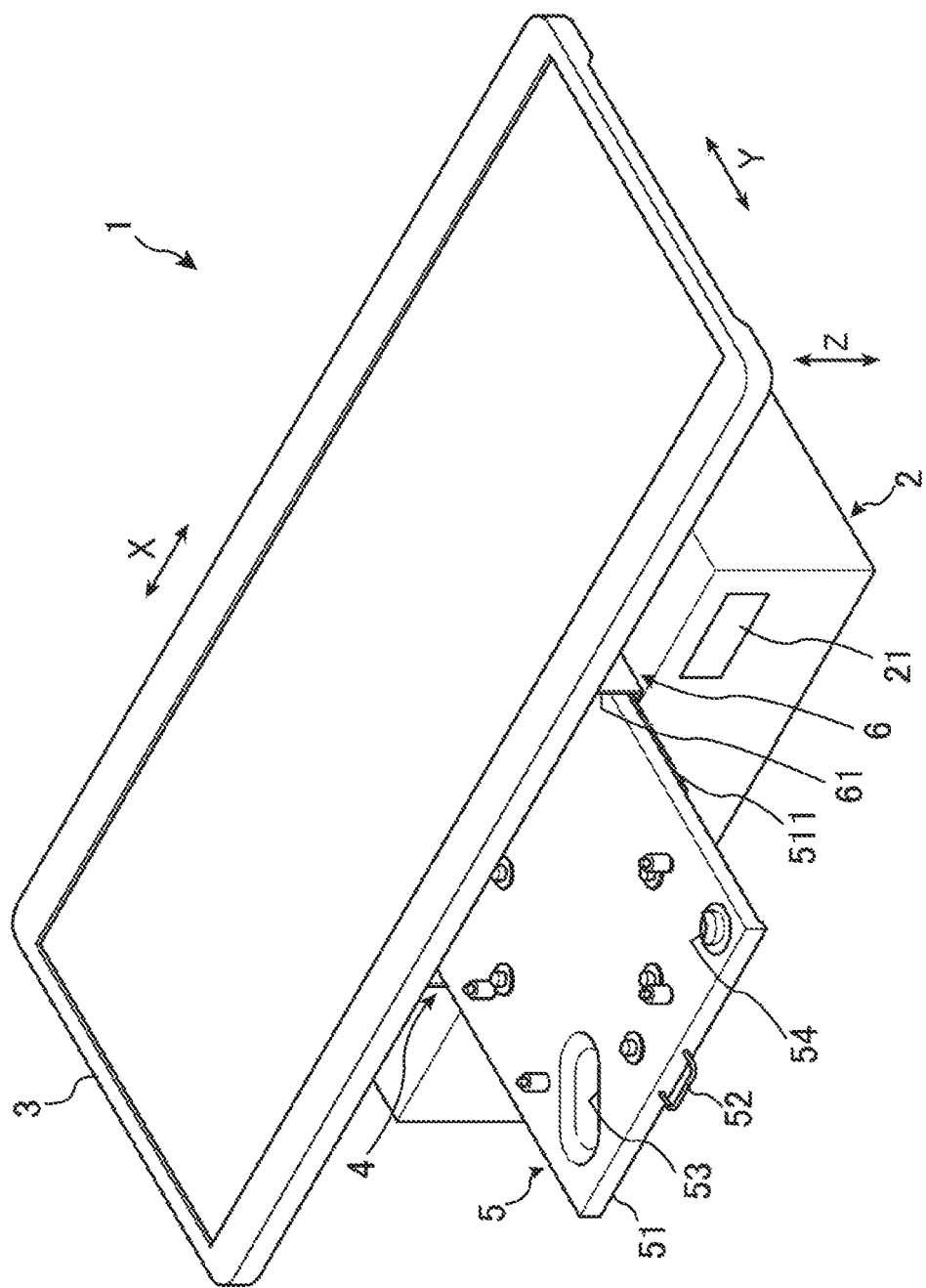
FIG. 1 is a perspective view illustrating an external form of a bucky image capturing table according to one or more embodiments.

FIG. 1 is an external perspective view of a bucky image capturing table according to one or more embodiments.

In one or more embodiments, a bucky image capturing table 1 is configured to include a base 2 installed on a floor surface, a top plate 3 which is disposed on the base 2 and on which a subject is placed at the time of image capturing, and a panel holding portion which is disposed between the base 2 and the top plate 3 and is capable of loading an X-ray detection panel capable of detecting X-rays therein, and the like.

The bucky image capturing table 1 is provided with a moving mechanism (not illustrated) which moves the top plate 3 in a longitudinal direction (X direction of FIG. 1) and a width direction (Y direction of FIG. 1) of the top plate 3 orthogonal to the longitudinal direction, and is able to adjust the position of the top plate 3 in the plane direction.

Further, the bucky image capturing table 1 is provided with an elevating mechanism (not illustrated) which elevates the top plate 3 in a height direction (Z direction of FIG. 1), and is able to adjust the height from the floor surface of the top plate 3.

In one or more embodiments, as illustrated in FIG. 1, the description will be given of a case where the bucky image capturing table 1 is a bucky image capturing table for so-called supine position capturing, in which the radiation image capturing is performed with the subject lying on the top plate 3 or the like.

The bucky image capturing table 1 forms a radiation image capturing system (not illustrated) together with a bulb that emits radiation or a console (not illustrated) that is a control device.

The positions of the top plate 3 in the longitudinal direction (the X direction of FIG. 1), the width direction (the Y direction of FIG. 1), and the height direction (the Z direction of FIG. 1) are controlled and grasped by a control device such as a console, and the position or the angle of the bulb can be adjusted accordingly.

Figure 2:
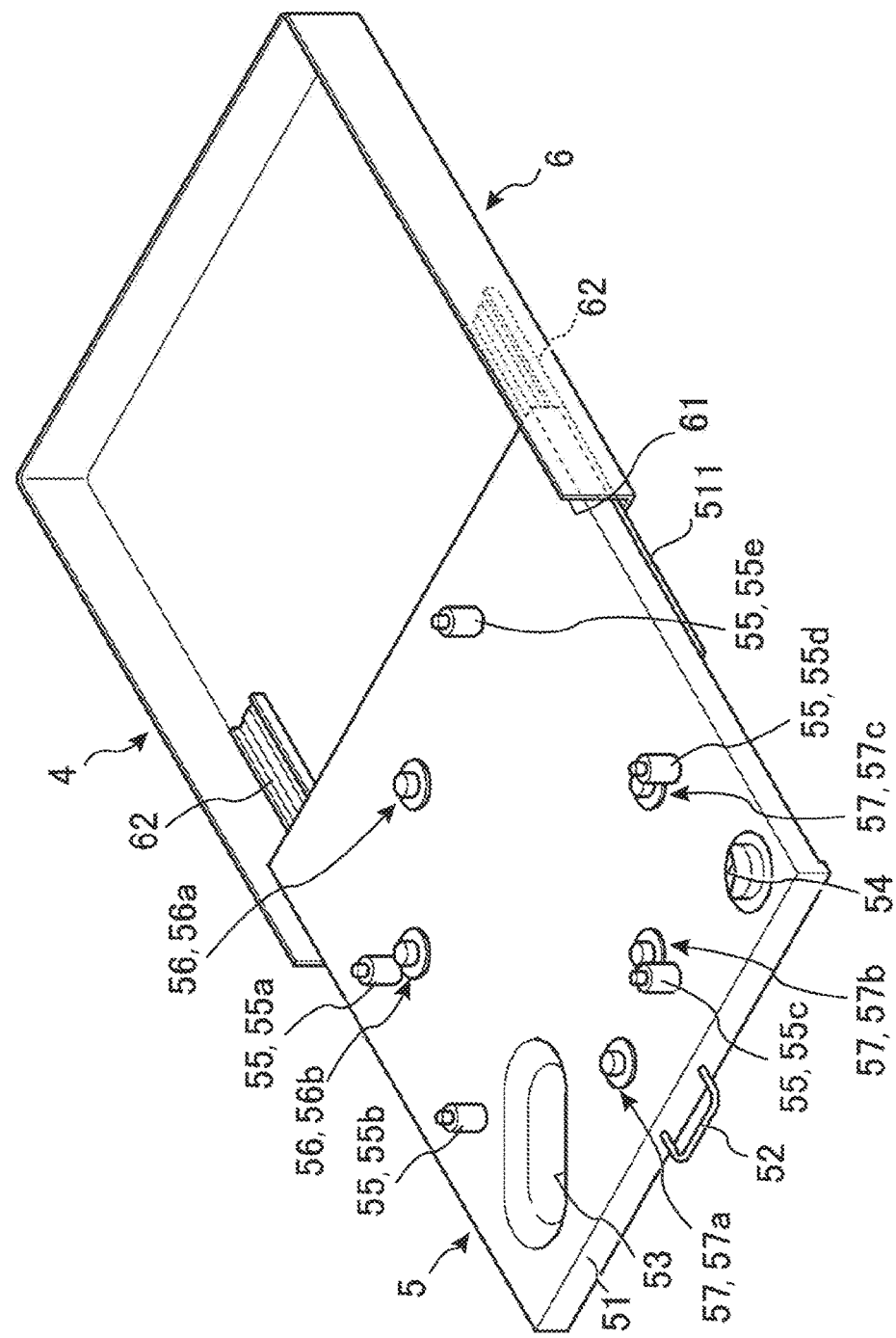
FIG. 2 is a perspective view of a panel holding portion of a bucky image capturing table according to one or more embodiments.

FIG. 2 is a perspective view of the cassette holder 4 according to one or more embodiments.

As illustrated in FIG. 2, the cassette holder 4 houses an X-ray detection panel P (see FIG. 3 or the like) therein.

As the X-ray detection panel P housed in the cassette holder 4, a CR cassette, an FPD cassette, or the like is assumed.

The CR cassette stores a stimulable phosphor sheet or the like inside a cassette-like housing, in a computed radiography (CR) apparatus using a stimulable phosphor sheet.

Further, the FPD cassette is a radiation image capturing apparatus (Flat Panel Detector) that detects the emitted radiation by a radiation detecting element to acquire the radiation image data as digital image data, and is a portable radiation image capturing apparatus which stores the radiation detecting element or the like inside a housing to be portable.

The cassette holder 4 serving as a panel holding portion is configured to include a holding tray 5 that holds the X-ray detection panel P, a main body portion 6 that houses the holding tray 5, and the like.

The main body portion 6 is formed in a housing shape in which an opening 61 is provided on one side (that is, one of the right and left side surface portions of the bucky image capturing table 1) in the width direction (Y direction of FIG. 1) of the bucky image capturing table 1.

In one or more embodiments, the holding tray 5 is inserted into the main body portion 6 from the opening 61 along the width direction (Y direction of FIG. 1) of the bucky image capturing table 1.

Specifically, the holding tray 5 can be inserted into and extracted from the main body portion 6 in the following manner.

That is, a pair of base side rails 62 is provided on the inner bottom surface of the main body portion 6 in one or more embodiments to extend in the width direction (Y direction of FIG. 1) of the bucky image capturing table 1. On the lower surface of the holding tray 5 and at a position corresponding to the base side rail 62, a slide side rail 511 to be locked slidably along the extending direction of the base side rail 62 is provided, and when the slide side rail 511 moves to slide along the base side rail 62, the holding tray 5 can be inserted into and extracted from the main body portion 6.

In the opening 61 of the main body portion 6, a door portion that can be opened and closed by a hinge or the like may be provided. In this case, when the X-ray detection panel P is loaded and stored in the main body portion 6, and the door portion is closed, the opening 61 is closed and the X-ray detection panel P is stored inside the main body portion 6.

Figure 3:
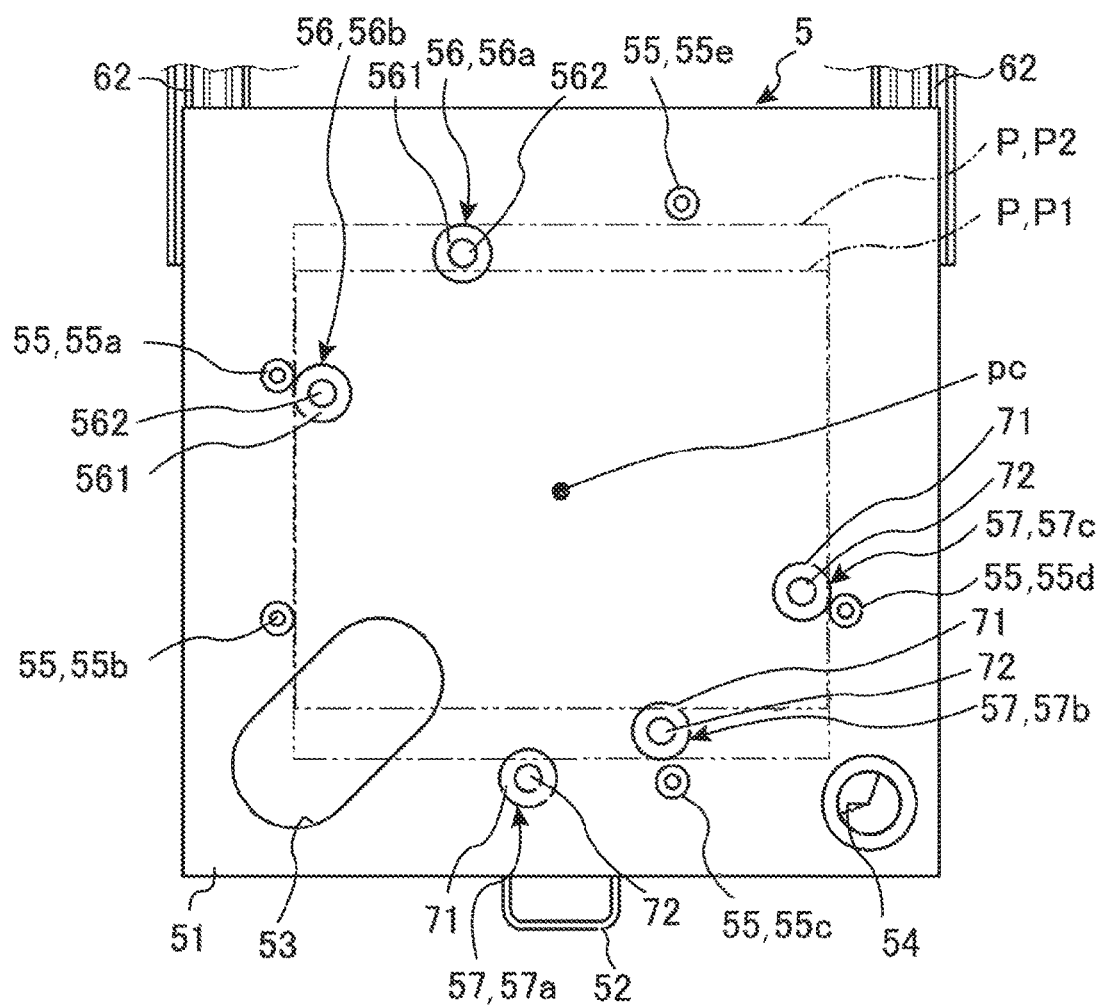
FIG. 3 is a plan view illustrating a holding tray of the panel holding portion according to one or more embodiments.

FIG. 3 is a plan view of the holding tray 5 in one or more embodiments.

The holding tray 5 holds the X-ray detection panel P on the placing surface thereof.

As illustrated in FIGS. 2 and 3, the holding tray 5 of one or more embodiments has a flat plate-like tray main body 51, and a handle 52 is provided on the front side in the insertion direction of the tray main body 51 (that is, the extending direction of the slide side rail 511).

The upper surface of the tray main body 51 serves as a placing surface for holding the X-ray detection panel P, and holds the X-ray detection panel P on its upper surface (placing surface).

A recessed portion 53 is provided on the left side in front (in one or more embodiments, the lower side illustrated in FIG. 3) of the insertion direction of the tray main body 51 (that is, the extending direction of the slide side rail 511).

The recessed portion 53 is provided to make the work easier, by inserting fingers between the tray main body 51 and the X-ray detection panel P, when the X-ray detection panel P is set on the tray main body 51 or when the X-ray detection panel P is detached from the top of the tray main body 51.

Further, in one or more embodiments, a case where the recessed portion 53 is provided on the front left side of the tray main body 51 in the insertion direction is illustrated, but the recessed portion 53 may be located at a position where a finger is easily inserted between the tray main body 51 and the X-ray detection panel P, and a specific arrangement is not particularly restricted.

Further, the tray main body 51 may have any shape in which a finger is easily inserted between the tray main body 51 and the X-ray detection panel P, and its shape is not limited to the illustrated example.

Further, in the tray main body 51 of one or more embodiments, a cable opening portion 54 is provided on the right side of the front side (in one or more embodiments, the lower part illustrated in FIG. 3) in the insertion direction (that is, the extending direction of the slide side rail 511) is provided.

In a case where the X-ray detection panel P placed on the tray main body 51 of one or more embodiments is an FPD cassette, as it will be described later, a cable (a cable 50 in FIGS. 9 and 10) for receiving power supply from an external power source (not illustrated) can be connected to a connector 59 (see FIGS. 9 and 10) of the X-ray detection panel P. The cable opening portion 54 is a through-hole through which the cable 50 is inserted when the image capturing is performed in a state in which the cable 50 is connected to the FPD cassette serving as the X-ray detection panel P.

Although the above embodiments illustrate a case where the cable opening portion 54 is provided on the front right side of the insertion direction of the tray main body 51, the cable opening portion 54 may be configured to smoothly extract the cable 50 connected to the X-ray detection panel P (FPD cassette) to the outside of the tray main body 51, and the specific arrangement, the shape and the like are not particularly limited.

When the bucky image capturing table 1 applies only the CR cassette as the X-ray detection panel P (that is, when the X-ray detection panel P does not assume the connection of the cable 50), it is possible to adopt a configuration in which the cable opening portion 54 is not provided.

The holding tray 5 is provided with a lock capable of locking the X-ray detection panel P on the placing surface (that is, the upper surface of the tray main body 51) with a plurality of holding patterns of X-ray detection panels P having different kinds and arrangement directions thereof, and a detector capable of detecting the holding pattern of the X-ray detection panel P locked on the placing surface.

Here, the type of the X-ray detection panel P of one or more embodiments is the size of the X-ray detection panel P. Here, an example is illustrated in which two types of the sizes (the length of the vertical and horizontal sides) of a rectangle of 14×17 inches and a square of 17×17 inches when the FPD cassette P is viewed in a plan are applicable.

In FIG. 3 and the like, the X-ray detection panel P having the size of 14×17 inches is referred to as an X-ray detection panel P1, and the square X-ray detection panel P having the size of 17×17 inches is referred to as an X-ray detection panel P2.

Further, when merely referred to as an X-ray detection panel P, it is assumed that both the rectangular X-ray detection panel P1 and the square X-ray detection panel P2 are included.

Further, the arrangement direction of the X-ray detection panel P is an orientation when the X-ray detection panel P is disposed on the placing surface (that is, the upper surface of the tray main body 51).

In the rectangular X-ray detection panel P1, it is possible to obtain three patterns of arrangement directions. The three patterns of arrangement directions include a horizontal arrangement in which the X-ray detection panel P1 is set so that the longer side (that is, a side of a length of 17 inches) is disposed along the width direction (Y direction of FIG. 1) of the bucky image capturing table 1, a vertical arrangement in which the X-ray detection panel P1 is set so that the longer side (that is, the side of a length of 17 inches) is disposed along the longitudinal direction (X direction of FIG. 1) of the bucky image capturing table 1, and a diagonal arrangement in which the X-ray detection panel P1 is rotated by 45° clockwise or counterclockwise (counterclockwise in one or more embodiments, see FIG. 9) from the vertical arrangement state.

Further, in the square X-ray detection panel P2, it is possible to obtain two patterns of arrangement directions. The two patterns of arrangement directions include a normal arrangement in which the X-ray detection panel P1 is set such that one side is arranged along the longitudinal direction (X direction of FIG. 1) of the bucky image capturing table 1, and a diagonal arrangement in which the X-ray detection panel P1 is rotated by 45° clockwise or counterclockwise (counterclockwise in one or more embodiments, see FIG. 10) from the normal arrangement state.

In this way, in the one or more embodiments, two types are used as the type of the X-ray detection panels P in which three types are used as the arrangement direction of the rectangular X-ray detection panel P1, and two types are used as the arrangement direction of the square X-ray detection panel P2. Thus, the X-ray detection panel P can be held on the holding tray 5 with a total of five types of holding patterns.

The specific configuration thereof will be described below.

On the surface of the tray main body 51 (that is, a surface on which the X-ray detection panel P is placed), a protrusion as a lock for positioning and locking the X-ray detection panel P is provided to abut against the side portion of the X-ray detection panel P in a state of protruding to the surface (on the placing surface) of the tray main body 51.

At least a part of the protrusion is a retractable and movable protrusion in which an upper end portion on the protruding side is buried to the same height as the placing surface (the surface of the tray main body 51) when the X-ray detection panel P is placed on the protrusion, and the upper end portion is in a protruded state of protruding from the placing surface (the surface of the tray main body 51) when the X-ray detection panel P is not placed. The specific configuration of the movable protrusion 56 is not particularly limited.

In one or more embodiments, as illustrated in FIGS. 2 and 3, as the lock, five locking protrusions 55 (fixed protrusions 55a to 55e) serving as the protrusions in the state of always protruding to the surface (on the placing surface) of the tray main body 51, and two movable protrusions 56 (movable protrusions 56a and 56b) are arranged on the surface (placing surface) of the tray main body 51.

Further, three sensors 57 (sensors 57a to 57c) are provided as a detector on the surface of the tray main body 51 (that is, the surface on which the X-ray detection panel P is placed).

Figure 4:
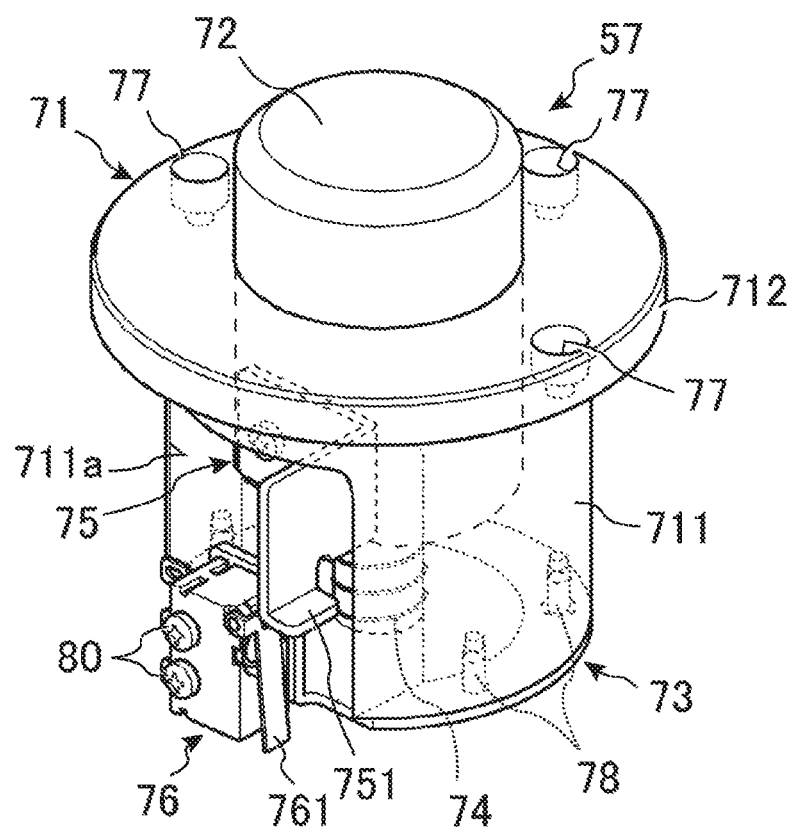
FIG. 4 is a perspective view of a sensor according to one or more embodiments.
Figure 5:
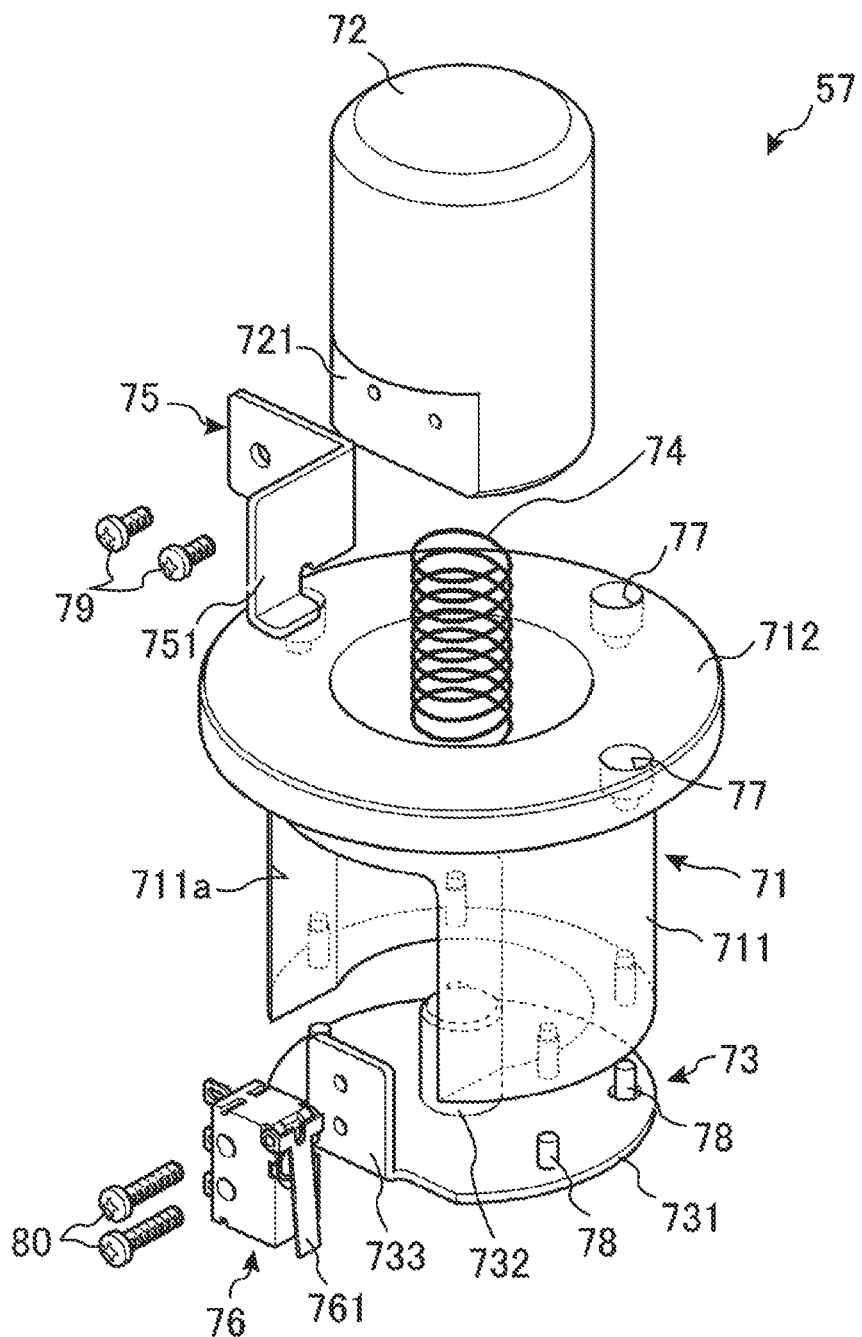
FIG. 5 is an exploded perspective view of the sensor.

FIG. 4 is a perspective view of the sensor, and FIG. 5 is an exploded perspective view of the sensor.

As illustrated in FIGS. 4 and 5, the sensor 57 of one or more embodiments includes an exterior part 71, a movable part 72 disposed in the exterior part 71, and a bottom plate 73 which forms the bottom part of the sensor 57. The bottom plate 73 is fixed to the exterior part 71 with a screw 78.

The exterior part 71 includes a hollow cylindrical part 711, and a flange part 712 provided on the upper end surface of the cylindrical part 711.

The side surface of the cylindrical part 711 is partially notched to form an opening portion 711a.

Further, the flange part 712 is fixed to the tray main body 51 with a screw 77 (see FIGS. 6A and 6B)

A coil spring 74 as an urging member for urging the movable part 72 in an upward direction (the upward direction of FIGS. 4 and 5) is disposed on the bottom plate 73. The movable part 72 is urged in the upward direction by the coil spring 74, and in a state in which the X-ray detection panel P is not placed, the movable part 72 is in a protruded state of protruding from the placing surface (the surface of the tray main body 51).

The coil spring 74 is set at a reaction force to the extent that the movable part 72 is lowered by the weight of the X-ray detection panel P. As the X-ray detection panel P is placed, the movable part 72 reliably descends.

Further, when the X-ray detection panel P is removed from the top of the movable part 72, the movable part 72 returns to a position at which the movable part 72 becomes a protruded state by the reaction force of the coil spring 74.

A contact member 75 having a contact part 751 is fixed to the lower part of the movable part 72 at a position corresponding to the opening portion 711a, with a screw 79.

Further, on the bottom plate 73, a switch fixing part 733 is provided at a position corresponding to the opening portion 711a, and a switch part 76 having a switch tongue piece 761 is fixed to the switch fixing part 733, with a screw 80.

The contact part 751 attached to the movable part 72 comes into contact with the switch tongue piece 761 of the switch part 76 when the movable part 72 is lowered by placing the X-ray detection panel P on the sensor 57, and thus, the switch part 76 is turned on.

FIG. 6A is a front view of the sensor in a state in which the X-ray detection panel is not placed, and FIG. 6B is a front view of the sensor in a state in which the X-ray detection panel is placed.

As illustrated in FIG. 6A, in a state in which the X-ray detection panel P is not placed, the movable part 72 of the sensor 57 is in a protruded state of protruding upward from the flange part 712.

In this state, the contact part 751 of the movable part 72 is at a position of not coming into contact with the switch tongue piece 761 of the switch part 76, and the switch part 76 is turned off.

In contrast, when the X-ray detection panel P is placed on the sensor 57, the movable part 72 is pressed down in a direction of an arrow illustrated in FIG. 6A against the urging force of the coil spring 74, by the weight of the X-ray detection panel P.

As a result, as illustrated in FIG. 6B, the movable part 72 descends, the contact part 751 comes into contact with the switch tongue piece 761 of the switch part 76, and thus, the switch part 76 is turned on.

When the switch part 76 is turned on, the switching signal is sent to a control unit (not illustrated) of the bucky image capturing table 1. As a result, the control unit can grasp that any one of the sensors 57a to 57c is turned on, and the ON/OFF state of the switch part 76.

Further, as it will be described later, the control unit may identify that the X-ray detection panel P is held on the holding tray 5 from the pattern of the ON/OFF state of the switch part 76 by which type of holding pattern, or whether none of the X-ray detection panels P is placed.

The control unit for identifying the holding status of the X-ray detection panel P by receiving the switching signal from the switch part 76 is not limited to one provided in the bucky image capturing table 1, and may be a control device, such as a console, which generally controls the radiation imaging system.

Further, in the lowered state of the movable part 72, the upper surface of the movable part 72 is located substantially at the same height as the upper end surface of the flange part 712. Since the lower part of the sensor 57 portion from the flange part 712 is disposed so as to be buried in the interior of the tray main body 51, when the movable part 72 is located substantially at the same height as the upper end surface of the flange part 712, the upper surface of the sensor 57 portion is substantially flush with the surface of the tray main body 51 (that is, the surface on which the X-ray detection panel P is placed). Therefore, the X-ray detection panel P is stably supported on the tray main body 51 without rattling.

Although FIGS. 6A and 6B illustrate a case where the flange part 712 is brought into contact with the upper surface of the tray main body 51 so as to be covered from the upper side and is fixed with a screw, the configuration for fixing the flange part 712 to the tray main body 51 is not limited thereto.

For example, a configuration in which the flange part 712 is brought into contact with the upper surface of the tray main body 51 from the lower side and is fixed with a screw may be adopted.

In this case, an opening portion for protrusion of the movable part 72 of the sensor 57 is formed on the top surface of the tray main body 51 and at a position corresponding to the portion in which the sensor 57 is buried, and in a state in which the X-ray detection panel P is not placed, only the movable part 72 is configured to protrude on the upper surface of the tray main body 51. Further, when the X-ray detection panel P is placed on the sensor 57, the upper surface of the movable part 72 is substantially flush with the upper surface of the tray main body 51.

With such a configuration, when the X-ray detection panel P is placed on the sensor 57, it is possible to make the placing surface of the X-ray detection panel P in a more even state, and the X-ray detection panel P can be more stably supported on the tray main body 51.

Further, at least a part of the sensor 57 serving as the detector may also serve as the movable protrusion 56 described above.

That is, when the X-ray detection panel P is placed on the sensor 57, the movable part 72 descends to turn on the switch part, and functions as a detector for detecting that the X-ray detection panel P is placed. However, when the X-ray detection panel P is not placed on the sensor 57, the movable part 72 is in a state of protruding from the upper surface of the tray main body 51, and in this protruded state, the movable part 72 may function as a lock which is brought into contact with the side portion of the X-ray detection panel P to position and lock the X-ray detection panel P.

Further, the movable protrusion 56 may have the same configuration as the sensor 57 except that it does not have the contact member 75 including the switch part 76 and the contact part 751 for switching the switch part 76. By making the members common in this way, it is possible to expect simplification of the component manufacturing process and reduction of the device cost.

Here, with reference to FIGS. 7A to 7E, the states of the holding pattern of the X-ray detection panel P held by the holding tray 5 in one or more embodiments, the protrusions (the fixed protrusions 55a to 55e and the movable protrusions 56a and 56b) serving as a lock in each holding pattern, and the sensors 57a to 57c as the detector will be described.

FIGS. 7A to 7C are plan views illustrating the positional relation between each arrangement direction of the X-ray detection panel of 14×17 size, and the protrusions serving as the lock and the sensors serving as the detector. FIGS. 7D and 7E are plan views illustrating the positional relation between each arrangement direction of the X-ray detection panel of 17×17 size, and the protrusions and the sensors.

As illustrated in FIG. 7A, when a rectangular X-ray detection panel P1 having lengths of the vertical and horizontal sides of 14×17 inches is horizontally disposed such that the longer side (that is, a side having a length of 17 inches) is disposed along the width direction (Y direction of FIG. 1) of the bucky image capturing table 1, only the sensor 57b is located under the X-ray detection panel P1, the movable part 72 of the sensor 57b is pressed down and is lowered until it is substantially flush with the surface of the tray main body 51, and only the switch part 76 of the sensor 57b is turned on. Further, the movable protrusion 56a is also located under the X-ray detection panel P1 and is pressed down until the protruding portion is substantially flush with the surface of the tray main body 51.

At this time, the fixed protrusions 55c and 55e and the movable protrusion 56b are brought into contact with the side surface of the X-ray detection panel P1, and the X-ray detection panel P1 is positioned and fixed. Furthermore, the movable parts 72 of the sensor 57a and 57c of the sensor 57, on which the X-ray detection panel P1 is not placed, also function as the movable protrusion which comes into contact with the side surface of the X-ray detection panel P1 to position and fix the X-ray detection panel P1.

As illustrated in FIG. 7B, when the rectangular X-ray detection panel P1 having lengths of the vertical and horizontal sides of 14×17 inches is vertically disposed such that the longer side (side having a length of 17 inches) is disposed along the longitudinal direction (X direction of FIG. 1) of the bucky image capturing table 1, only the sensor 57c is located under the X-ray detection panel P1, the movable part 72 of the sensor 57c is pressed down and is lowered until the movable part 72 is substantially flush with the surface of the tray main body 51, and only the switch part 76 of the sensor 57c is turned on. Further, the movable protrusion 56b is also disposed under the X-ray detection panel P1, and is pressed down until the protruding portion is substantially flush with the surface of the tray main body 51.

Further, at this time, the fixed protrusions 55a, 55b, and 55d and the movable protrusion 56a are brought into contact with the side surface of the X-ray detection panel P1, thereby positioning and fixing the X-ray detection panel P1. Furthermore, the movable part 72 of the sensor 57b of the sensor 57, on which the X-ray detection panel P1 is not placed, also functions as a movable protrusion which comes into contact with the side surface of the X-ray detection panel P1 to position and fix the X-ray detection panel P1.

As illustrated in FIG. 7C, the rectangular X-ray detection panel P1 having the lengths of the horizontal and vertical sides of 14×17 inches is shifted to a diagonal arrangement rotated counterclockwise by 45° from the vertically arranged state in which the longer side (the side having a length of 17 inches) is disposed along the longitudinal direction (X direction of FIG. 1) of the bucky image capturing table 1, only the sensor 57a is disposed under the X-ray detection panel P1, the movable part 72 of the sensor 57a is pressed down to descend until the movable part 72 is substantially flush with the surface of the tray main body 51, and only the switch part 76 of the sensor 57a is turned on.

At this time, the fixed protrusions 55b and 55e and the movable protrusions 56a and 56b are brought into contact with the side surface of the X-ray detection panel P1 to position and fix the X-ray detection panel P1. Furthermore, the movable parts 72 of the sensors 57b and 57c of the sensor 57, on which the X-ray detection panel P1 is not placed, also function as a movable protrusion part which comes into contact with the side surface of the X-ray detection panel P1 to position and fix the X-ray detection panel P1.

Further, as illustrated in FIG. 7D, when a square X-ray detection panel P2 having the lengths of the vertical and horizontal sides of 17×17 inches is normally disposed such that one side is disposed along the longitudinal direction (X direction of FIG. 1) of the bucky image capturing table 1, the sensors 57b and 57c are located under the X-ray detection panel P2, the movable parts 72 of the sensors 57b and 57c are pressed down and lowered until the movable parts 72 are substantially flush with the surface of the tray main body 51, and the switch parts 76 of the sensors 57b and 57c are turned on. Also, the movable protrusions 56a and 56b are also located under the X-ray detection panel P2 and are pressed down until the protruding portion is substantially flush with the surface of the tray main body 51.

At this time, the fixed protrusions 55a, 55b, 55c, 55d, and 55e are brought into contact with the side surface of the X-ray detection panel P2 to position and fix the X-ray detection panel P2. Furthermore, the movable part 72 of the sensor 57a of the sensor 57, on which the X-ray detection panel P2 is not placed, also function as a movable protrusion which comes into contact with the side surface of the X-ray detection panel P2 to position and fix the X-ray detection panel P2.

Further, as illustrated in FIG. 7E, a square X-ray detection panel P2 having the length of the horizontal and vertical sides of 17×17 inches is shifted to an oblique arrangement rotated by 45° counterclockwise from a normally arranged state in which one side is disposed along the longitudinal direction (X direction of FIG. 1) of the bucky image capturing table 1, the sensors 57a, 57b, and 57c are placed under the X-ray detection panel P2, all the movable parts 72 of the sensors 57a, 57b, and 57c are pressed down and are lowered until the movable parts 72 are substantially flush with the surface of the tray main body 51, and the switch parts 76 of all the sensors 57a, 57b, and 57c are turned on. Also, the movable protrusions 56a and 56b are also placed under the X-ray detection panel P2 and are pressed down until the protruding portions are substantially flush with the surface of the tray main body 51.

Further, at this time, the fixed protrusions 55a, 55b, 55c, 55d, and 55e are brought into contact with the side surface of the X-ray detection panel P2 to position and fix the X-ray detection panel P2.

In this way, in one or more embodiments, all the types of the sensors 57 that are turned on are different from each other, depending on the type and arrangement direction of the X-ray detection panel P. Therefore, the control unit that receives the ON/OFF signal from the sensor 57 can easily determine that any type of X-ray detection panel P is set in the holding tray 5 in any direction, by grasping that any sensor 57 is turned on.

When any of the sensors 57 is turned off, it is determined that nothing is set in the X-ray detection panel P in the holding tray 5.

Further, in FIGS. 7A to 7E, the rotational center of the X-ray detection panel P is defined as a "rotational center pc".

In one or more embodiments, as illustrated in FIGS. 7A to 7E, the lock (that is, the fixed protrusions 55a to 55e, the movable protrusions 56a and 56b, and the like) are configured to position the X-ray detection panel P such that the rotational center pc of the X-ray detection panel P is the same in any holding patterns.

When the rotational center pc of the X-ray detection panel P changes, it is necessary to adjust the position or the angle of the bulb accordingly. In this way, in any of the holding patterns, by not shifting the rotational center pc of the X-ray detection panel P, it is possible to eliminate the troublesome work of re-adjusting the position and angle of the bulb each time the holding pattern changes.

Depending on only the arrangement of the lock (that is, the fixed protrusions 55a to 55e, the movable protrusions 56a and 56b, and the like) or the detector (that is, the sensors 57a to 57c), in some cases, it is difficult for the user to determine whether to dispose the X-ray detection panel P at any position in any holding pattern.

Figure 8:
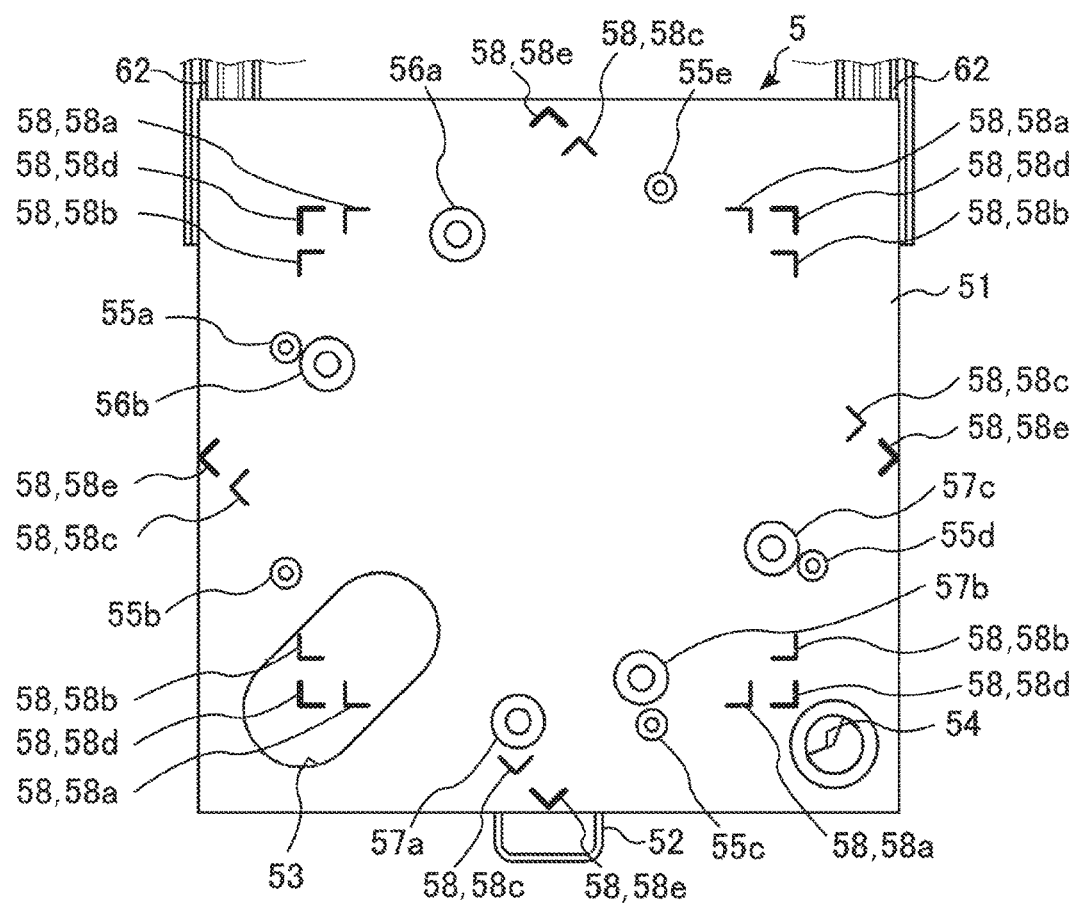
FIG. 8 is a plan view illustrating an example of a holding tray with a marker attached thereto according to one or more embodiments.

Therefore, for example, as illustrated in FIG. 8, a marker 58 indicating the arrangement of the X-ray detection panel P for each holding pattern may be provided on the surface or the like of the tray main body 51 of the holding tray 5.

The marker 58 can be performed by sealing, printing, or the like. The method of performing the marker on the surface or the like of the tray main body 51 is not limited to the one exemplified here.

In FIG. 8, the marker 58 in the case of horizontally arranging the rectangular X-ray detection panel P1 (in the case of the arrangement of FIG. 7A) is set as a marker 58a, the marker 58 in the case of horizontally arranging the rectangular X-ray detection panel P1 (in the case of the arrangement of FIG. 7B) is set as a marker 58b, the marker 58 in the case of horizontally arranging the rectangular X-ray detection panel P1 (in the case of the arrangement of FIG. 7C) is set as a marker 58c, the marker 58 in the case of normally arranging the square X-ray detection panel P2 (in the case of the arrangement of FIG. 7D) is set as a marker 58d, and the marker 58 in the case of obliquely arranging the square X-ray detection panel P2 (in the case of the arrangement of FIG. 7E) is set as a marker 58e.

Further, the marker 58 can be made more recognizable to the user by changing the color, the thickness, and the like for each holding pattern.

Figure 9:
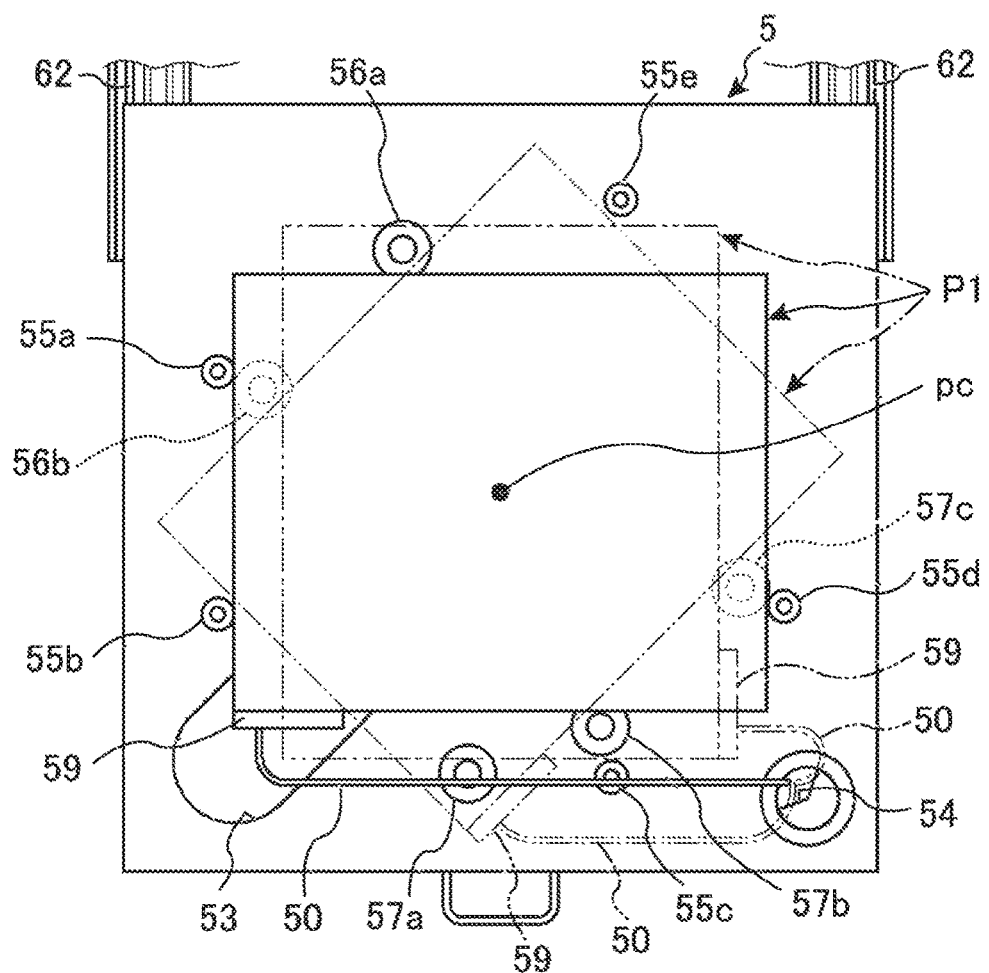
FIG. 9 is a schematic plan view illustrating a connector position of X-ray detection panel of 14×17 size and a wiring situation of a cable according to one or more embodiments.
Figure 10:
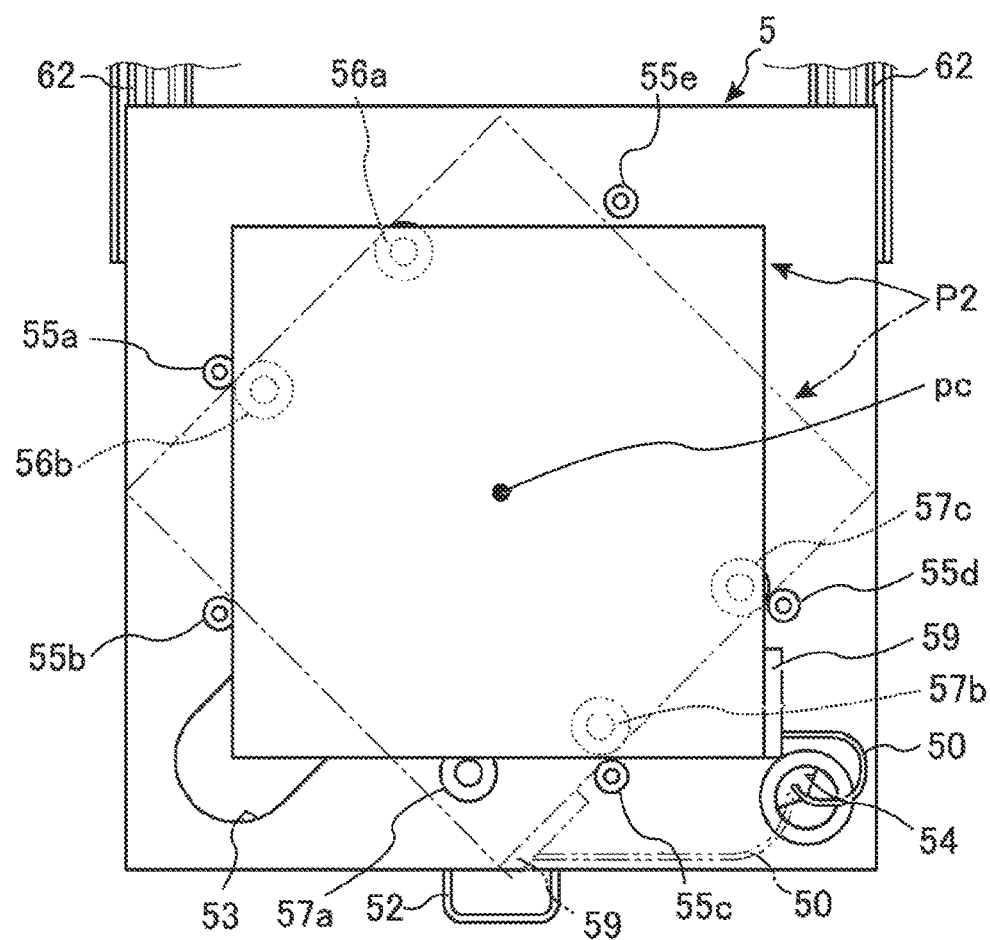
FIG. 10 is a schematic plan view illustrating a connector position of an X-ray detection panel of 17×17 size and a wiring situation of a cable according to one or more embodiments.

FIGS. 9 and 10 illustrate arrangement examples of the X-ray detection panel P in a case where the X-ray detection panel P includes a connector 59, and the X-ray detection panel P is a wire-connectable panel (for example, an FPD cassette) connected to an external device by connecting the cable 50 to the connector 59.

FIG. 9 illustrates an example of a case where the X-ray detection panel P is a rectangular X-ray detection panel P1, and FIG. 10 illustrates an example where the X-ray detection panel P is a square X-ray detection panel P2.

As illustrated in FIGS. 9 and 10, in a case where the X-ray detection panel P is a wire-connectable panel equipped with the connector 59, even when the X-ray detection panel P is held by any holding pattern, the X-ray detection panel P is arranged at a position where the connector 59 does not interfere with the lock (that is, the fixed protrusions 55a to 55e, the movable protrusions 56a and 56b, and the like) or the detector (that is, the sensors 57a to 57c).

With such an arrangement, it is possible to prevent erroneous ON/OFF information from being output as the connector 59 rides on the sensors 57a to 57c.

Further, it is possible to prevent the connector 59 from hitting the fixed protrusions 55a to 55e, the movable protrusions 56a and 56b, and the sensors 57a to 57c to cause damage to either or both of them.

Further, in a case where the X-ray detection panel P is a wire-connectable panel equipped with the connector 59, as illustrated in FIGS. 9 and 10, the X-ray detection panel P is arranged such that the connector 59 is positioned on the side close to the proximal end side of the cable 50 in any holding pattern.

In one or more embodiments, the position at which the cable opening portion 54 is provided is the proximal end side of the cable 50 connected to the external device.

Therefore, in one or more embodiments, as illustrated in FIGS. 9 and 10, the X-ray detection panel P is arranged such that the distance between the connector 59 and the cable opening portion 54 is the shortest distance in any holding pattern.

Further, since the holding tray 5 is housed in the main body portion 6 of the cassette holder 4 at the time of image capturing, it is possible to check that which type of X-ray detection panel P is arranged in the holding tray 5 in any orientation (attitude).

Therefore, when a detection signal obtained by detecting the holding pattern of the X-ray detection panel P locked on the placing surface of the holding tray 5 is output from the sensor 57 serving as the detector of the holding tray 5, a notifier for providing notification of the holding pattern is provided.

For example, the notifier can be provided as a display such as an indicator which displays the holding pattern of the X-ray detection panel P held on the placing surface of the holding tray 5 by letters, figures, or the like, on the basis of the detection signal that is output from the sensor 57.

In one or more embodiments, as illustrated in FIG. 1, a display 21 such as an indicator is provided on the bucky image capturing table 1, and the display 21 may display that the X-ray detection panel P is set in the holding tray 5 in any type and any arrangement direction.

When displaying the type and arrangement direction of the X-ray detection panel P, using the display 21 as the notifier, the displaying method of the X-ray detection panel P and the like is not particularly limited, and may be easily understood by the user.

FIGS. 11A to 11D illustrate an example of displays in the display 21.

For example, the type and arrangement direction of the X-ray detection panel P may be displayed on the display 21 by letters. In this case, for example, letters corresponding to the type and arrangement direction of the current X-ray detection panel P are displayed in red, others are displayed in black, only letters corresponding to the type and arrangement direction of the current X-ray detection panel P are lighted up brightly, and others are turned off or darkened to distinguish.

Figure 11A:
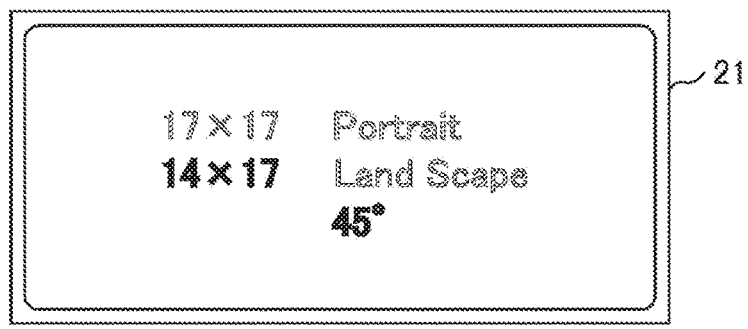
FIGS. 11A to 11D are diagrams illustrating display examples of indicators of the bucky image capturing table.
Figure 11B:
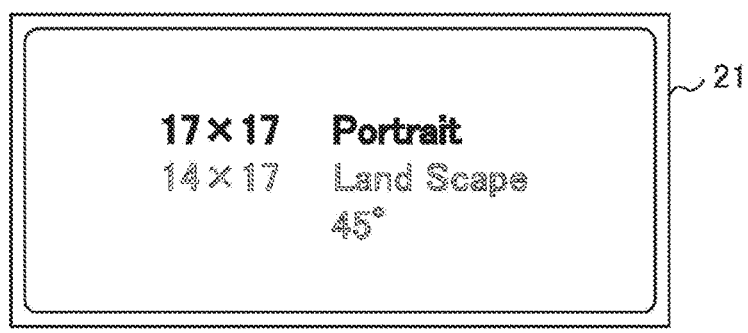

FIG. 11A illustrates a display example in a case where a rectangular X-ray detection panel P1 of 14×17 is obliquely arranged. Further, FIG. 11B illustrates a display example in a case where the square X-ray detection panel P2 of 17×17 is normally arranged.

According to this, the user can easily check the type and arrangement direction of the current X-ray detection panel P, by simply looking at the letters displayed on the display 21.

Further, for example, the type and arrangement direction of the current X-ray detection panel P may be represented by figures.

Figure 11C:
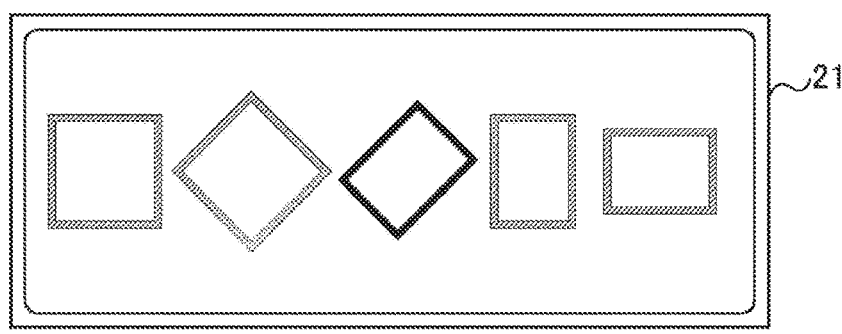

FIG. 11C illustrates an example in which figures illustrating the holding pattern of the X-ray detection panel P are displayed side by side, and only those corresponding to the type and arrangement direction of the current X-ray detection panel P are distinguished by changing colors or turning on the display. Further, FIG. 11D illustrates an example in which the figures illustrating the holding pattern of the X-ray detection panel P are arranged at one position in a superimposed manner, and only those corresponding to the type and arrangement direction of the current X-ray detection panel P are distinguished from other ones by turning on the display or changing the colors.

Figure 11D:
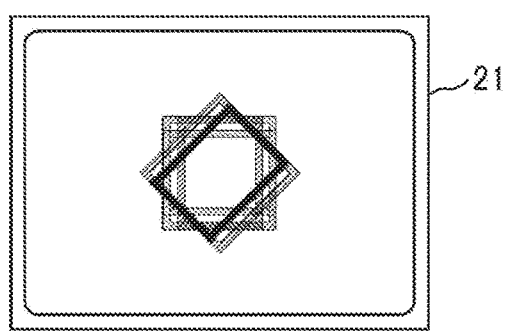

Further, in the case of being displayed by figures as illustrated in FIGS. 11C and 11D, it is possible to expect that the user more intuitively grasps the type and arrangement direction of the current X-ray detection panel P as compared to the case of being displayed by letters.

Further, the notifier is not limited to the display 21, and may be, for example, an element which notifies the user by voice, alarm, or the like.

Next, operations and effects of the holding tray 5 and the bucky image capturing table 1 equipped with the holding tray 5 in one or more embodiments will be described.

The holding tray 5 of one or more embodiments is provided with the sensors 57*a* to 57*c* which are switched to output an ON signal when the X-ray detection panel P is placed thereon, as the detector, and the lock (that is, the fixed protrusions 55*a* to 55*e*, the movable protrusions 56*a* and 56*b*, and the like) is configured to position and fix the X-ray detection panel P at a position where the ON/OFF patterns of the sensor 57 are different from each other for each holding pattern of the X-ray detection panel P, as illustrated in FIGS. 7A to 7E.

Specifically, as illustrated in FIGS. 7A to 7E, the holding tray 5 corresponds to the rectangular X-ray detection panel P1 and the square X-ray detection panel P2, and the sensors 57 are turned into ON/OFF with different patterns to correspond to the three types of arrangement of the horizontal arrangement, the vertical arrangement, and the diagonal arrangement for the X-ray detection panel P1 and the two types of arrangements of the normal arrangement and the diagonal arrangement for the X-ray detection panel P2.

Therefore, it is possible to detect the unset state of a plurality of types (five types in one or more embodiments) of holding patterns and the X-ray detection panel P, by simply arranging a plurality (three in one or more embodiments) of sensors 57 of simple configuration, without a complicated and expensive configuration for rotating the holding tray 5 itself, a precise configuration for detecting the type or arrangement of the arbitrarily placed X-ray detection panel P, and the like.

With such a configuration of the holding tray 5, it is possible to set the image capturing range up to the length obtained by diagonally arranging the X-ray detection panel P2 of 17×17-inch size, and it is possible to set the femur having a maximum size in the human bone up to a person of about 180 cm in height, within the image capturing range, by diagonally arranging the commercially available X-ray detection panel P.

This also makes it possible to simplify the configuration of the bucky image capturing table 1, and even in a case where the X-ray detection panel P is held in any type of holding pattern, the position, angle, or the like of the bulb can be adjusted to an appropriate one according to the holding pattern of the X-ray detection panel P, and it is possible to perform the radiation image capturing of high-definition and high-quality.

Further, in one or more embodiments, the lock includes protrusions (fixed protrusions 55*a* to 55*e*, and movable protrusions 56*a* and 56*b*) which are brought into contact with the side portion of the X-ray detection panel P in a state of protruding on the placing surface to position the X-ray detection panel P.

For this reason, a simple configuration can be obtained, and the user can easily and quickly position the X-ray detection panel P, merely by disposing the X-ray detection panel P at a position that does not ride on the protrusion.

Since at least a part of the protrusions serving as a lock are the movable protrusions 56*a* and 56*b*, the part can be made not to protrude from the placing surface of the holding tray 5 in accordance with the holding pattern of the X-ray detection panel P, and it is possible to flexibly cope with a large number of holding patterns, as compared with a case where all the lock are constituted by the fixed protrusions 55.

Further, the detector is retractable and movable detector in which, when at least a part of the sensor 57 (all the three sensors 57*a* to 57*c* in one or more embodiments) serving as the detector is placed on the X-ray detection panel P, the protruding side end portion is buried up to the same height as the placing surface, and when the X-ray detection panel P is not placed, the protruding side end portion is in a protruded state of protruding from the placing surface.

Therefore, the sensor 57 on which the X-ray detection panel P is not mounted can be made to function as a movable protrusion, and the positioning and locking of the X-ray detection panel P can be performed efficiently, without increasing the number of members.

Further, in one or more embodiments, as illustrated in FIGS. 7A to 7E and the like, the X-ray detection panel P is positioned such that the rotational center pc of the X-ray detection panel P is the same in any of the holding patterns.

Therefore, it is not necessary to adjust the position and angle of the bulb for each holding pattern of the X-ray detection panel P, and preparation for image capturing can be performed easily and quickly.

Further, since the X-ray detection panel P includes the connector 59, the holding tray 5 of one or more embodiments can also cope with the case of the X-ray detection panel P such as a wire-connectable FPD cassette connected to the external device by connecting the cable 50 to the connector 59.

By connecting the cable to the FPD cassette so that electric power supplied from an external power source can be received, the image capturing can be performed without worrying about the remaining battery power.

Further, in one or more embodiments, in a case where the X-ray detection panel P is a wire-connectable panel such as FPD cassette, even when the X-ray detection panel P is held by any holding pattern, the connector 59 is disposed at a position which does not interfere with the lock (that is, the fixed protrusions 55a to 55e, and the movable protrusions 56a and 56b) and the detector (that is, the sensors 57a to 57c). As a result, malfunction of the sensor 57 can be prevented, and it is possible to prevent damage to the lock and the detector due to interference with the connector 59.

Further, in one or more embodiments, when the X-ray detection panel P is a wire-connectable panel such as an FPD cassette, the X-ray detection panel P is arranged such that the connector 59 is positioned on the side close to the proximal end side of the cable 50 in any holding pattern.

Therefore, it is possible to suppress the interference of the cable 50 with the lock (that is, the fixed protrusions 55a to 55e, and the movable protrusions 56a and 56b) and the detector (that is, the sensors 57a to 57c), thereby improving the routing of the cable 50.

Further, in one or more embodiments, the sensor 57 serving as the detector outputs a detection signal (that is, ON signal when the switch part 76 is switched) when the holding pattern of the X-ray detection panel P locked on the placing surface is detected.

Therefore, the holding pattern of the X-ray detection panel P can be output to the control unit of the bucky image capturing table 1 or other external device, thereby accurately performing the control or the like of the bulb.

One or more embodiments illustrate an example in which the fixed protrusions 55a to 55e and the movable protrusions 56a and 56b are included as the lock, and the sensors 57a to 57c are included as the detector, but the configuration and arrangement of the lock (the position and the number to be arranged) and the configuration and arrangement of the detector (the position and the number to be arranged) are not limited to those exemplified herein.

In a case where only the rectangular X-ray detection panel P1 of 14×17 is used as the type of the X-ray detection panel P, since there are also three types of holding patterns, the holding pattern of the X-ray detection panel P can be detected even when the number of the lock or the detector is smaller than the case of the above embodiments.

Further, although the detector of the above embodiments was adopted as the sensor 57 which can also serve as the movable protrusion, the detector is not limited thereto. For example, the detector may be a contact sensor or the like buried in the tray main body 51.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A holding tray that holds an X-ray detection panel on a placing surface, the holding tray comprising:
   a lock that locks the X-ray detection panel on the placing surface with a plurality of holding patterns of different types and/or arrangement directions of the X-ray detection panel; and
   a detector that detects the holding pattern of the X-ray detection panel locked on the placing surface.

2. The holding tray according to claim 1, wherein
   the detector comprises three sensors, and
   the lock is a protrusion that comes into contact with a side portion of the X-ray detection panel in a state of protruding on the placing surface to position and lock the X-ray detection panel.

3. The holding tray according to claim 2, wherein
   at least a part of the protrusion is a retractable and movable protrusion in which a protruding side end portion is buried up to a same height as the placing surface when the X-ray detection panel is placed on the protrusion, and
   the protruding side end portion is in a protruded state of protruding from the placing surface when the X-ray detection panel is not placed.

4. The holding tray according to claim 3, wherein
   at least a part of the detector is a retractable and movable detector in which a protruding side end portion is buried up to the same height as the placing surface when the X-ray detection panel is placed on the detector, and
   the protruding side end portion of the detector is in a protruded state of protruding from the placing surface when the X-ray detection panel is not placed.

5. The holding tray according to claim 1, wherein the lock positions the X-ray detection panel such that a rotational center of the X-ray detection panel is the same in any of the holding patterns.

6. The holding tray according to claim 1, wherein the X-ray detection panel is a wire-connectable panel that includes a connector, and is connected to an external device by connecting a cable to the connector.

7. The holding tray according to claim 6, wherein the connector is disposed at a position that does not interfere with the lock and the detector when the X-ray detection panel is held by any of the holding patterns.

8. The holding tray according to claim 6, wherein the X-ray detection panel is arranged such that the connector is positioned on a side close to a proximal end side of the cable in any of the holding patterns.

9. The holding tray according to claim 1, wherein the detector outputs a detection signal when detecting the holding pattern of the X-ray detection panel locked on the placing surface.

10. A bucky image capturing table comprising:
    the holding tray according to claim 1; and
    a top plate disposed between the X-ray detection panel held by the holding tray at a time of image capturing and a subject as an image capturing target to support the subject.

11. The bucky image capturing table according to claim 10, further comprising:
    a notifier that provides notification of the holding pattern when a detection signal is obtained by detecting the holding pattern of the X-ray detection panel held on the placing surface of the holding tray from the detector of the holding tray.

12. The bucky image capturing table according to claim 11, wherein the notifier is a display that displays the holding pattern of the X-ray detection panel held on the placing surface of the holding tray by letters and/or figures, on the basis of the detection signal output from the detector.

* * * * *